US00PP31467P2

(12) United States Plant Patent
Hansen

(10) Patent No.: US PP31,467 P2
(45) Date of Patent: Feb. 18, 2020

(54) ***SALVIA* PLANT NAMED 'VIOLET PROFUSION'**

(50) Latin Name: ***Salvia nemorosa* (Linnaeus)**
Varietal Denomination: Violet Profusion

(71) Applicant: Hans A Hansen, Zeeland, MI (US)

(72) Inventor: Hans A Hansen, Zeeland, MI (US)

( * ) Notice: Subject to any disclaimer, the term of this patent is extended or adjusted under 35 U.S.C. 154(b) by 0 days.

(21) Appl. No.: 16/350,490

(22) Filed: Nov. 21, 2018

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 6/00; A01H 5/02; A01H 6/508
See application file for complete search history.

*Primary Examiner* — Keith O. Robinson

(57) ABSTRACT

A new and distinct cultivar of perennial *Salvia* plant named 'Violet Profusion' characterized by its violet-blue flowers in densely arranged in verticils with greyish purplish-red calyces and matching bracts. The new plant has a compact habit with stiff, upright, heavily-branched stems with strong tendency to repeat when deadheaded, a strong vigorous growth rate and rugose gray-green foliage.

1 Drawing Sheet

Botanical classification: *Salvia nemorosa* (Linnaeus);
Cultivar designation: 'Violet Profusion';

STATEMENT REGARDING PRIOR DISCLOSURES UNDER 37 CFR 1.77(b)(6)

The first public disclosure of the claimed plant, in the form of a sale, was made by Walters Gardens, Inc. on Apr. 10, 2018. Prior to that, on Dec. 1, 2017 the claimed plant was displayed with a photograph and brief description in a website operated by Walters Gardens, Inc., who obtained the plant and all information relating thereto, from the inventor. No plants of *Salvia* 'Violet Profusion' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of ornamental sage plant hereinafter referred to by the cultivar name *Salvia* 'Violet Profusion' or as the new plant. The new plant was selected from an insect-pollinated cross between the female parent, an unreleased proprietary hybrid known only by the breeder code 12-98-1 (not patented) and an unnamed unreleased sibling of 12-98-1 (not patented) in May of 2013 at an isolation block at a wholesale perennial nursery in Zeeland, Mich. Seeds were collected in June of 2013 and the new plant begun the trial phase in the summer of 2015 and eventually assigned the breeder code 13-64-130 prior to assigning a cultivar name.

The new *Salvia* was further evaluated and asexually propagated first by division in 2015, then propagated by basal cuttings were taken at the same nursery in Zeeland, Mich., USA in June of 2016. Evaluation of these and further cutting grown plants shows that *Salvia* 'Violet Profusion' continues to be stable and produce true to type plants in successive generations of asexual propagation.

SUMMARY OF THE INVENTION

Plants of *Salvia* 'Violet Profusion' can be most closely compared to *Salvia* 'Indiglo Girl' U.S. Plant patent application Ser. No. 15/998,377, 'Violet Riot' U.S. Plant Pat. No. 26,273, 'May Night' ('Mainacht') (not patented) and 'Midnight Model' U.S. Plant Pat. No. 29,498. All of the above mentioned cultivars are taller in habit. The flowers of 'Indiglo Girl' are larger and the petals are less violet, larger basal leaves, and the calyces are greener. The flowers of 'Violet Riot' are more violet in color. 'May Night' has flowers that are lighter colored, taller in habit and the calyces are not as deeply colored. 'Midnight Model' is taller in habit, larger basal foliage, produces less repeat flowering when deadheaded, and the flower color is a darker strong violet shade. 'Bumbleblue' U.S. Plant Pat. No. 30,084 is shorter in habit and flower color is slightly different. 'Sensation Blue' (not patented) has shorter habit and the flowers are slightly lighter in hue. Neither parent was physically maintained nor was photography maintained, so no comparison of the parents is possible.

The following characteristics in combination distinguish *Saliva* 'Violet Profusion' as a new and distinct cultivar from all other cultivars known to the inventor:

1. Violet-blue flowers densely arranged in dense verticils;
2. Stiff, upright, heavily-branched flower stems;
3. Strong repeat flowering when deadheaded;
4. Compact, rounded, strong, vigorous and winter-hardy habit;
5. Rugose gray-green foliage.

BRIEF DESCRIPTION OF THE DRAWINGS

The photographs of the new plant demonstrate the unique traits and the overall appearance of *Salvia* 'Violet Profusion'. The colors are as accurate as reasonably possible with color reproductions. Variation in ambient light spectrum, source and direction may cause the appearance of minor variation in color. The plant used in the photographs was a two-year-old plant grown in an open, full-sun trial garden at a wholesale perennial nursery in Zeeland, Mich. with supplemental water and fertilizer when needed.

DETAILED BOTANICAL DESCRIPTION

Figure 1:
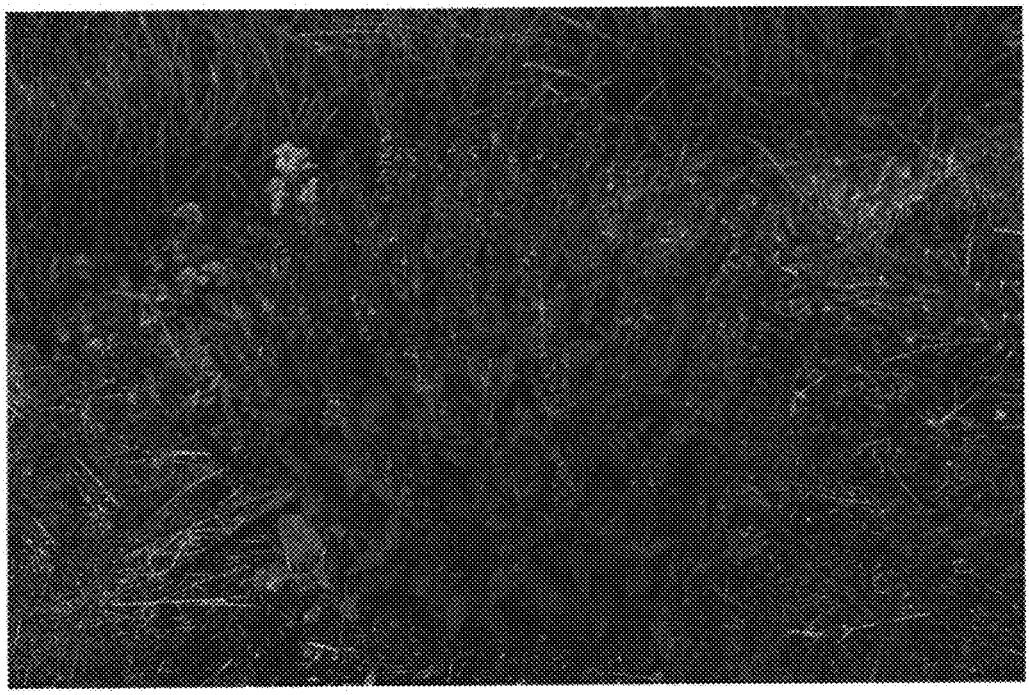
FIG. 1 shows the plant habit in full flower in a landscape.
Figure 2:
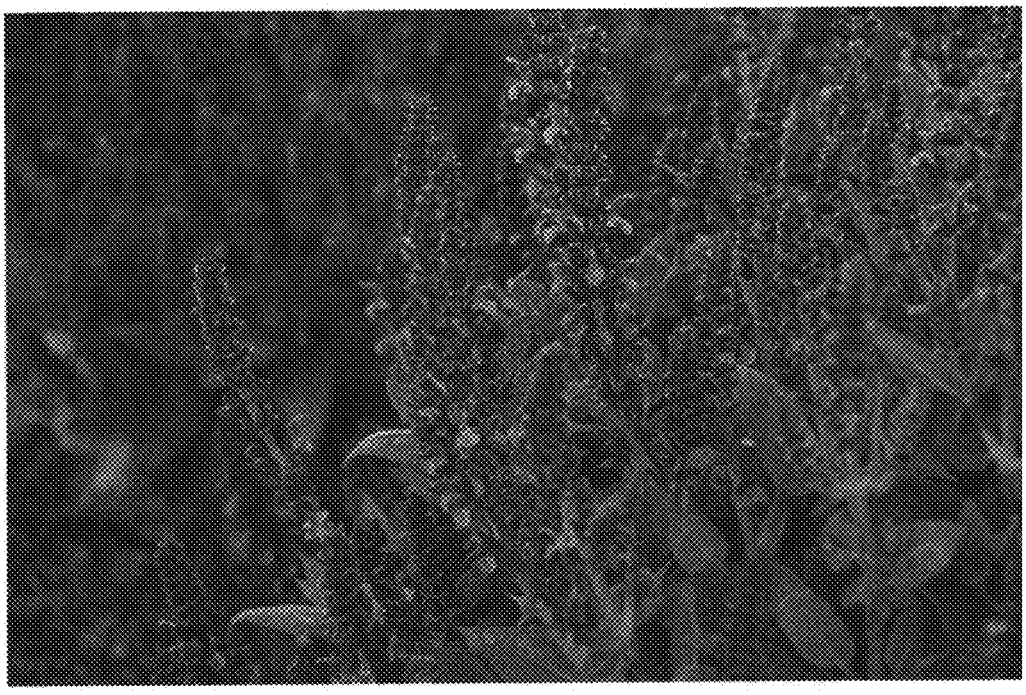
FIG. 2 shows a close-up of the flower scapes with the buds, flowers, stems and calyxes.

The following descriptions and color references except where common dictionary terms are used are based on the 2015 edition of The Royal Horticultural Society Colour Chart. *Salvia* 'Violet Profusion' has not been observed under all possible environments. The phenotype may vary slightly with different growing environments such as temperature, light, fertility, soil pH, moisture and plant maturity levels, but without any change in the genotype. The following observations and size descriptions are based on three-year-old plants growing in an outdoor full-sun trial garden and in a greenhouse at a wholesale perennial nursery in Zeeland, Mich. and greenhouse forced two-year old plants. Plants were given supplemental water and fertilizer.

Parentage: Female or seed parent the unreleased hybrid 12-98-1; the male or pollen parent is a sibling to 12-98-1;

Plant habit: Winter-hardy herbaceous perennial; multi-stemmed, compact, rounded, with basal and cauline foliage, and flowers in several, tightly-arranged verticils on highly-branched upright racemes displayed above foliage; flowering to about 45.0 cm tall and about 70.0 cm wide at the fullest point about 25 cm above soil; with cauline foliage below branches;

Propagation: By basal vegetative shoot cuttings; time to produce a rooted stems about two weeks;

Growth rate: Rapid, vigorous, finishing in a 65 mm container in about 7 weeks from rooted cutting, and from 65 mm container to flowering 3.8 liter container in about 8 weeks.

Root description: Fine, well-branched; color dependent on age and soil type, from cream to dark tan in color; typically nearest RHS 161D;

Foliage: Opposite, simple, rugose, lanceolate; margin crenate; glabrous and matte abaxial and adaxial surfaces; acute apex and base cordate to rounded; leaf blades about 10.0 cm long and 4.5 cm across, decreasing in size distally; average about 7.5 cm long and 2.8 cm across; faint sage fragrance; variegation absent;

Foliage color: Adaxial surface nearest RHS 137A; abaxial surface nearest RHS 138A; expanding foliage nearest RHS 146B adaxial and abaxial;

Venation: Reticulate; impressed on adaxial side and costate on abaxial side; abaxial midrib sparsely puberulent, secondary veins glabrous; adaxial puberulent;

Vein color: Adaxial midrib nearest RHS 145D, secondary veins same as leaf; abaxial midrib nearest RHS 146D and primary and secondary veins nearest RHS 146C;

Petiole: Concavo-convex; puberulent adaxial and abaxial and ciliolate margin distally and ciliate proximally; to about 10.5 cm long and 5.0 mm wide, average 6.0 cm long and 4.0 mm wide at base;

Petiole color: Adaxial nearest RHS 146C and abaxial nearest RHS 146D;

Inflorescence description: Perfect, bilabiate, verticillate with flowering generally beginning at lower verticils and advancing up the scape, but not all flowers at each verticil opening at the same time giving the effect of a scape being in continuous flower for longer periods; average distance between verticils about 1.5 mm, greater proximally and less distally; self-cleaning, petals not persistent; flowering beginning late spring for about six weeks and repeating if initial scapes removed; total length about 45 cm long, flowering in upper 15 cm and branching to about 7 cm wide; average internode distance in flowering portion about 6.0 mm; number of flowers per node or verticil about 12 in lowest nodes, decreasing distally;

Inflorescence attitude: With midline projected about 20 degree angle above horizontal and hood petal about 40 degree angle above horizontal;

Flower longevity: About four days on the plant;

Fragrance: None detected under present growing conditions;

Flower buds one day prior to anthesis: Shape is rounded on top and slightly concave below, with rounded apex; micro-puberulent; about 8.0 mm long, 3.5 mm tall and 2.5 mm wide;

Bud color: Exposed dorsal petals between RHS 86A and RHS N88A, ventral petals nearest RHS 90A; calyx nearest RHS N79B;

Flowers: Bilabiate corolla with arcuate hooded upper lip and tri-lobed lower lip; about 16.0 mm long, 10.5 mm tall and 6.0 mm wide, fused into corolla tube in the proximal 6.0 mm; clustered at verticils with up to 8 flowers per verticil;

Petals: Bilabiate corolla; upper hood petal and flattened side to side vertically, with emarginate apex and base fused with labium;

Hood (upper) petal: Minutely puberulent outside, glabrous inside; about 13.0 mm long, 3.0 mm tall and 2.0 mm across;

Labium (lower) petal: Consisting of three lobes, two proximal lobes projecting outwardly, about 2.0 mm long and 1.5 mm wide near middle with rounded to sub-acute apex; center lobe reflex; rounded apex, about 5.0 mm long 6.5 mm wide; center lobe slightly concaved upwards; total labium about 11.0 mm long, 6.5 mm wide at the widest portion across middle of central lobe and 5.0 mm tall;

Petal color: Adaxial hood petal nearest RHS N88A, abaxial nearest RHS N88B distally and toward margin and nearest RHS N88D toward lower center; lower labium petal proximal lobes abaxial and adaxial nearest RHS N88B and center lobe adaxial nearest RHS N88A and abaxial nearest RHS N89C; adaxial and abaxial fused corolla lighter than RHS 85D;

Androecium: Two, fused with labium, contained within hood petal except when triggered by pollinator;

*Filament*.—Cylindrical; glabrous, fused about 5.0 mm from base of labium petal; curved around inside of hood petal; about 1.5 mm long and less than 0.3 mm diameter with a 1.0 mm trip mechanism at base; color between RHS 76C and RHS 76D; trip lever color between RHS 76C and RHS 76D.

*Anther*.—Glabrous, oblong, about 1.5 mm long and 1.0 mm diameter; longitudinal, dorsifixed; color nearest RHS N187A.

*Pollen*.—Abundant; globose; less than 0.1 mm circumference; color nearest RHS 7D.

Gynoecium: One, curved around inside of hood petal;

*Style*.—About 14.0 mm long and less than 0.5 mm diameter; color NN155D in basal 2.0 mm and gradually darkening distally to nearest RHS 79C just before stigma split.

*Stigma*.—Bifurcate and curved in the terminal 2.0 mm; apex pointed; color nearest RHS N79A.

*Ovary*.—Superior; color nearest RHS N144A.

Fruit: Nutlet, one to four per flower; rounded, about 1.5 mm diameter; color nearest RHS 202A;

Calyx: Five sepals, three upper and two lower, campanulate; apices acute; fused in basal 3.5 mm tube, about 6.0 mm long and 5.0 mm tall at mouth and 3.0 mm wide; lower set bifurcate in terminal 2.5 mm; upper set of trifurcate in distal 0.5 mm; glandular abaxial and glabrous adaxial;

Calyx color: Variable with light intensity, abaxial bases in little direct sunlight nearest RHS 145B with veins with regions of high light intensity veins and distally becoming nearest RHS 187A, abaxial regions receiving intense light nearest RHS N186C; adaxial base in low light nearest RHS 145C with veins and distal region or nearest RHS 146A adaxial base in regions of high light nearest RHS 145D with veins of nearest RHS 137B and distal regions of high light nearest 187A;

Bracts: Each verticil subtended by two opposite nearly cordate bracts; apex typically acuminate, base truncate; lower bracts margin crenate and micro-ciliolate, upper bracts entire and micro-ciliolate; mostly flat to slightly cupped distally; glabrous above and below; bract size up to 80.0 mm long and 8.0 mm wide, decreasing distally;

Bract color: Variable, adaxial and abaxial between RHS 185C and RHS 186C with veins nearest RHS 138A and apex nearest RHS 187A both abaxial and adaxial;

Peduncles: Raceme; quadrangular in cross section; about 15 to 25 per plant; strong; upright; to about 45.0 cm tall and 3.5 mm across at base, flowering in upper 15.0 cm and to about 3.5 cm across; puberulent; compound branches in lower two to four nodes, upright at 45 degrees above horizontal; branches to about 20.0 cm long and 3.0 mm across; average internode distance about 4.5 cm;

Peduncle color: Between RHS 138A and RHS 191A.

Pedicels: Cylindrical; micro-puberulent to glandular; about 1.5 mm long and 0.5 mm diameter; outwardly to slightly drooping at flower anthesis and with seed set;

Pedicel color: Nearest RHS 182B;

Disease and pest resistance: Resistant to diseases and pests beyond that common to *Salvia* has not been noted. Specific diseases have not been tested, but not commonly browsed by *Cervinae* or *Oryctolagus*.

Growth recommendations: Plants of *Salvia* 'Violet Profusion' perform best with adequate moisture and good drainage and are hardy from USDA zone 3 to 8.

It is claimed:

1. A new and distinct perennial *Salvia* plant named 'Violet Profusion' as herein described and illustrated useful for landscaping as a specimen plant or en masse.

* * * * *